United States Patent
Wang et al.

(10) Patent No.: US 11,708,381 B2
(45) Date of Patent: Jul. 25, 2023

(54) INHIBITORS OF ANDROGEN RECEPTOR SIGNALING

(71) Applicant: XAVIER UNIVERSITY OF LOUISIANA, New Orleans, LA (US)

(72) Inventors: Guangdi Wang, New Orleans, LA (US); Jiawang Liu, New Orleans, LA (US); Shilong Zheng, New Orleans, LA (US); Shanchun Guo, Tucker, GA (US)

(73) Assignee: XAVIER UNIVERSITY OF LOUISIANA, New Orleans, LA (US)

( * ) Notice: Subject to any disclaimer, the term of this patent is extended or adjusted under 35 U.S.C. 154(b) by 435 days.

(21) Appl. No.: 16/463,135

(22) PCT Filed: Nov. 22, 2017

(86) PCT No.: PCT/US2017/063004
§ 371 (c)(1),
(2) Date: May 22, 2019

(87) PCT Pub. No.: WO2018/098270
PCT Pub. Date: May 31, 2018

(65) Prior Publication Data
US 2021/0284663 A1 Sep. 16, 2021

Related U.S. Application Data

(60) Provisional application No. 62/426,368, filed on Nov. 25, 2016.

(51) Int. Cl.
*C07F 5/02* (2006.01)
*C07C 235/56* (2006.01)
*C07C 255/60* (2006.01)

(52) U.S. Cl.
CPC .............. *C07F 5/02* (2013.01); *C07C 235/56* (2013.01); *C07C 255/60* (2013.01)

(58) Field of Classification Search
CPC ...................................................... C07F 5/02
See application file for complete search history.

(56) References Cited

U.S. PATENT DOCUMENTS 5,994,335 A 11/1999 Brodie
2011/0105445 A1* 5/2011 Njar ..................... A61K 31/568
514/170

FOREIGN PATENT DOCUMENTS

WO 2013030410 A2 3/2013

OTHER PUBLICATIONS

Siegel, R., et al., "Cancer statistics, 2013," CA Cancer J Clin., (Jan. 2013) vol. 63, No. 1, 11-30.
Attard, G., et al., "New strategies in metastatic prostate cancer: targeting the androgen receptor signaling pathway," Clin Cancer Res. (Apr. 2011), vol. 17, No. 7, 1649-57.
Carver, B.S. "Strategies for targeting the androgen receptor axis in prostate cancer," Drug Discov Today. (Sep. 2014), vol. 19, No. 9, 1493-7.
Hoang, David T., et al., "Androgen receptor-dependent and -independent mechanisms driving prostate cancer progression: Opportunities for therapeutic targeting from multiple angles," Oncotarget, (2017), vol. 8, No. 2, 3724 -3745.
Lieberman, Ronald. "Androgen deprivation therapy for prostate cancer chemoprevention: current status and future directions for agent development," Urology, (Aug. 2001), vol. 58, 2 Suppl 1, 83-90.
Dhawan, Mallika, et al., "Utility of novel androgen receptor therapies in the real world: A nuanced approach," Urol Oncol., (Aug. 2016), vol. 34, No. 8, 340-7.
Graham, Laura, et al., "Targeting persistent androgen receptor signaling in castration-resistant prostate cancer," Med Oncol., (May 2016), vol. 33, No. 44, 1-17.
Crona, DJ., et al., "Androgen receptor targeting drugs in castration-resistant prostate cancer and mechanisms of resistance," Clin Pharmacol Ther. (Dec. 2015) vol. 98, No. 6, 582-9.
Modena, Alessandra, et al., "Metastatic castration-resistant prostate cancer: targeting the mechanisms of resistance to abiraterone acetate and enzalutamide," Expert Rev Anticancer Ther. (2015), vol. 15, No. 9, 1037-48.
Reichert, Zachery, et al. "Androgen Receptor and Beyond, Targeting Androgen Signaling in Castration-Resistant Prostate Cancer," Cancer J. (Sep./Oct. 2016), vol. 22, No. 5, 326-329.
Mamura, Yusuke, et al., "Androgen receptor targeted therapies in castration-resistant prostate cancer: Bench to clinic," Int J Urol. (Aug. 2016), vol. 23, No. 8, 654-65.
Mostaghel, Elahe, et al., "Resistance to CYP17A1 inhibition with abiraterone in castration-resistant prostate cancer: induction of steroidogenesis and androgen receptor splice variants," Clin Cancer Res (2011) vol. 17, 5913-25.
Galletti, Giuseppe, et al., "Mechanisms of resistance to systemic therapy in metastatic castration-resistant prostate cancer," Cancer Treat Rev. (Jun. 2017) vol. 57, 16-27.
Bubley, Glenn J., et al., "Association Between Androgen Receptor Splice Variants and Prostate Cancer Resistance to Abiraterone and Enzalutamide," J Clin Oncol (Jul. 1, 2017), vol. 35, No. 19, 2103-2105.
Antonarakis, Emmanuel S., et al., "AR-V7 and resistance to enzalutamide and abiraterone in prostate cancer," N Engl J Med (Sep. 11, 2014) vol. 371, No. 11, 1028-38.
Schrader, Andres J., et al, "Re: androgen receptor splice variants mediate enzalutamide resistance in castration-resistant prostate cancer cell lines," Eur Urol (2013) vol. 64, 169-70.

(Continued)

*Primary Examiner* — Nizal S Chandrakumar
(74) *Attorney, Agent, or Firm* — McBee Moore & Vanik IP, LLC; Chester G. Moore

(57) ABSTRACT

The present disclosure relates to androgen receptor signaling inhibitors and the synthesis of the same. Further, the present disclosure teaches the utilization of the androgen receptor signaling inhibitors in a treatment for proliferative diseases, including cancer, particularly prostate cancer, and especially castration-resistant prostate cancer.

21 Claims, 10 Drawing Sheets

(56) References Cited

OTHER PUBLICATIONS

Zhang, Xiaotun, et al., "Androgen receptor variants occur frequently in castration resistant prostate cancer metastases," PLoS One (2011), vol. 6, No. 11, e27970.

Sun, Shihua, et al., "Castration resistance in human prostate cancer is conferred by a frequently occurring androgen receptor splice variant," J Clin Invest (2010) vol. 120, No. 8. 2715-30.

Clement, Omoshile, et al., "Three dimensional pharmacophore modeling of human CYP17 inhibitors. Potential agents for prostate cancer therapy " J Med Chem (2003) vol. 46, No. 12, 2345-2351.

Bruno, Robert D., et al., "Synthesis and biological evaluations of putative metabolically stable analogs of VN/124-1 (TOK-001): head to head anti-tumor efficacy evaluation of VN/124-1 (TOK-001) and abiraterone in LAPC-4 human prostate cancer xenograft model." Steroids. (2011) vol. 76, No. 12, 1268-1279.

Njar, Vincent, et al., "Novel 17-azolyl steroids, potent inhibitors of human cytochrome 17 alpha-hydroxylase-C17,20-lyase (P450(17) alpha): potential agents for the treatment of prostate cancer." J Med Chem., (1998) vol. 41, No. 6, 902-912.

Njar, Vincent, et al., "Discovery and development of Galeterone (TOK-001 or VN/124-1) for the treatment of all stages of prostate cancer," J Med Chem., (2015), vol. 58, No. 5, 2077-2087.

International Search Report of International Patent Application No. PCT/US2017/063004 dated Apr. 6, 2018.

\* cited by examiner

INHIBITORS OF ANDROGEN RECEPTOR SIGNALING

CROSS-REFERENCE TO RELATED APPLICATIONS

This application is a National Stage entry of International Application No. PCT/US2017/063004, filed 22 Nov. 2017, which claims priority to U.S. Patent Application No. 62/426,368, filed 25 Nov. 2016. The disclosures of the priority applications are incorporated in their entirety herein by reference.

STATEMENT REGARDING FEDERALLY SPONSORED RESEARCH OR DEVELOPMENT

This invention was made with government support under grant number 2G12MD007595 awarded by the National Institute on Minority Health and Health Disparities (NIMHD). The government has certain rights in the invention.

BACKGROUND

1. Field

The present disclosure relates to small molecule agents that inhibit or block androgen receptor (AR) signaling by acting through suppression of androgen levels, by antagonizing the androgen receptor, or by down regulating the androgen receptor. The disclosure also relates to pharmaceutical compositions comprising these inhibitors, and methods for using the same for treatment of estrogen receptor mediated pathological developments, including cancers.

The AR signaling inhibitors described here can provide effective hormone therapy for prostate cancers, in particular those that have progressed to a state of castration resistance that continue to depend on, or influenced by AR signaling. The agents described here can be used to treat castration naïve prostate cancer, castration resistant prostate cancer (CRPC), or any other cancers sensitive to AR signaling, either as a first-line therapy or in a second line setting, as a monotherapeutic agent or in combination with other therapeutic agents.

2. Description of Related Art

Globally, prostate cancer remains the second most frequently diagnosed cancer in men with over 1.1 million new cases diagnosed in 2012 [1]. Prostate cancer is the fifth leading cause of cancer death worldwide [1]. The development and progression of prostate cancer relies on the androgen receptor, and the majority of androgen-independent or hormone refractory prostate cancers express AR. The inhibition of AR activity through mechanisms in addition to androgen ablation, such as modulation of signal transduction pathways, may delay prostate cancer progression [2-4]. Surgical or medical androgen deprivation therapy (ADT) has been the primary treatment paradigm for men with advanced prostate cancer [5]. Surgical ADT is achieved through bilateral orchiectomy, while medical ADT may be achieved through the use of luteinizing hormone-releasing hormone (LH-RH) agonists or LH-RH antagonists, and both surgical and medical ADT have been shown to successfully palliate symptoms associated with metastatic PC. However, almost all treated patients develop resistance to androgen deprivation, resulting in the development of castration-resistant prostate cancer (CRPC).

Recent studies have shown that further hormonal manipulation can result in impressive disease control even after progression on ADT, and thus, many patients with CRPC would respond to further hormonal manipulation [6]. This was demonstrated in phase III randomized trials showing improved survival for patients receiving the CYP17 hydroxylase inhibitor abiraterone and the second-generation AR antagonist enzalutamide [7-10]. These drugs proved that AR remains a clinically relevant, druggable target in CRPC. However, clinical benefits of abiraterone and enzalutamide therapies are limited by the inevitable development of resistance to both drugs [11, 12].

Numerous mechanisms have been demonstrated to drive disease progression upon AR-targeted therapy [13], of which the truncated and constitutively active AR variants (AR-Vs) due to alternative mRNA splicing has emerged as an important and common driver of drug resistance as they are frequently upregulated in castration-resistant compared hormone-responsive tumor tissues [14-18]. The AR variants have lost the ligand binding domain (LBD) and are thus capable of ligand independent activation of androgen responsive element (ARE)-driven reporters in the absence of androgen. While AR-Vs confer ligand independence, AR signaling remains critical in the proliferation of CRPC, thus offering clinical opportunities for novel agents that can still target the AR signaling pathway.

BRIEF SUMMARY

Blocking AR signaling can be achieved by a variety of approaches. One such approach is to block the biosynthesis of testosterone by inhibiting the enzyme CYP17A1 which is responsible for converting pregnenolone to 17-hydroxypregnenolone and progesterone to 17-hydroxyprogesterone, key intermediates of testosterone biosynthesis.

Another approach is to block the androgen receptor directly using antagonists that competitively bind to AR or form covalent bond with the amino-terminal domain (NTD) of AR. Yet another approach is to use agents that downregulate the expression of AR and/or AR-Vs, in particular AR-V7, one of the most prevalent AR splice variants in hormone resistant prostate tumors. Additional approaches to interfere with AR signaling are being explored for therapeutic utilities.

Thus, in an embodiment, the AR targeting therapeutic agents of the present disclosure are compounds of the formula (I):

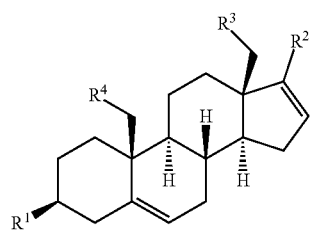

Formula I wherein:
R¹ is H, OH, OMe, F, CF$_3$, OCF$_3$, Cl, Br, (HO)$_2$B, KF$_3$B, NaF$_3$,

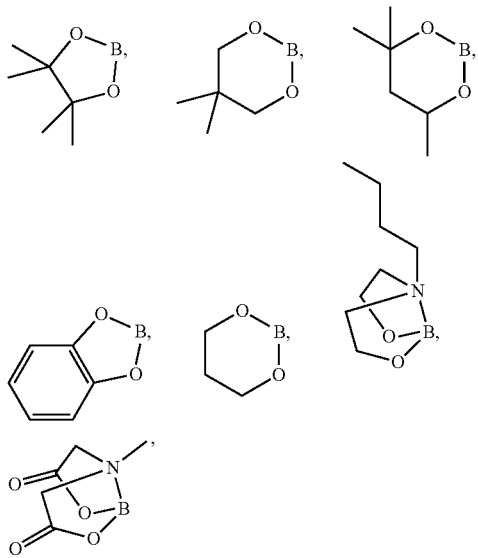

wherein if a boron atom is present in R¹ then the substituent point of attachment is on the boron atom;
R² is

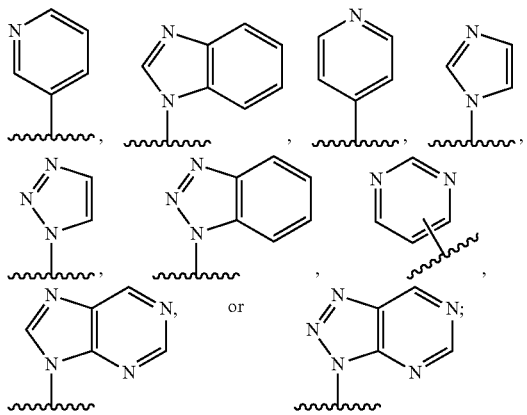

R³ is H or CH$_3$; and
R⁴ is H or CH$_3$.

Examples of compounds of Formula (I) are shown in FIGS. 1-3, for which the general synthetic schemes for synthesizing AR signaling inhibitors (ARi) of Formula (I) are described in detail.

In another embodiment, the AR targeting therapeutic agents of the present disclosure are ARi compounds of the formula (II):

Formula II

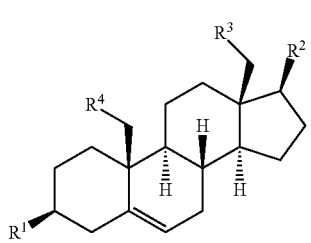

wherein:
R¹ is H, OH, OMe, F, CF$_3$, OCF$_3$, Cl, Br, (HO)$_2$B, KF$_3$B, NaF$_3$,

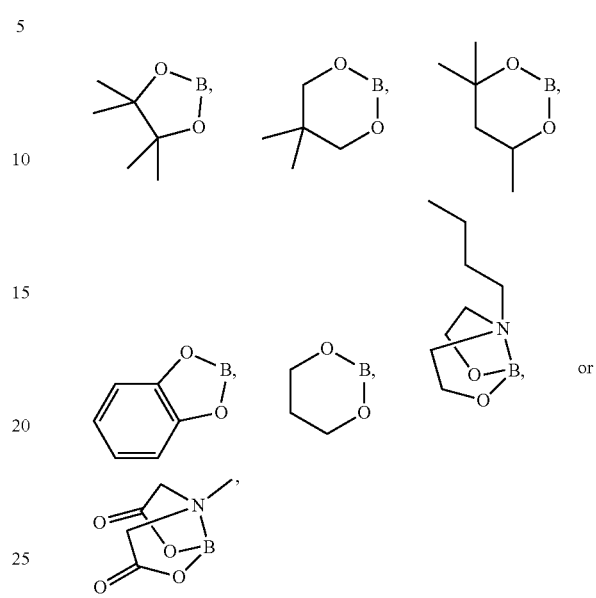

wherein if a boron atom is present in R¹ then the substituent point of attachment is on the boron atom;
R² is

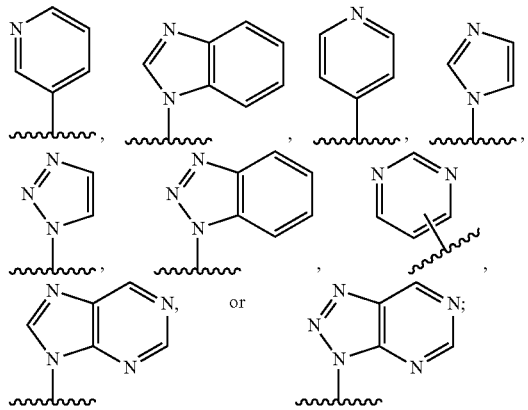

R³ is H or CH$_3$; and
R⁴ is H or CH$_3$.

In another embodiment, the AR targeting therapeutic agents of the present disclosure are ARi compounds of the formula (III):

Formula III

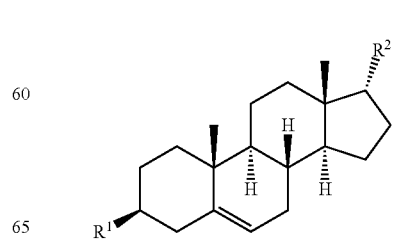

wherein:

R¹ is H, OH, OMe, F, CF₃, OCF₃, Cl, Br, (HO)₂B, KF₃B, NaF₃,

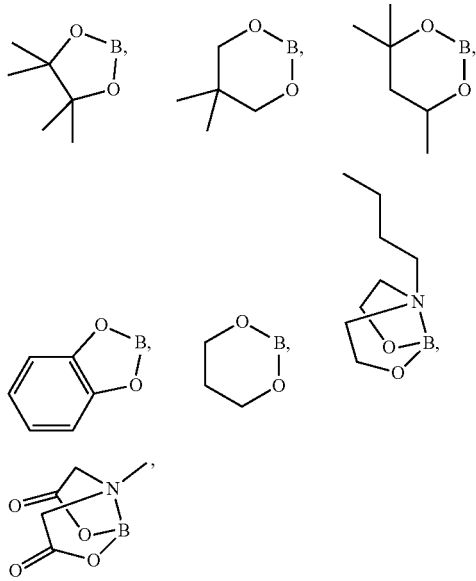

wherein if a boron atom is present in R¹ then the substituent point of attachment is on the boron atom;

R² is

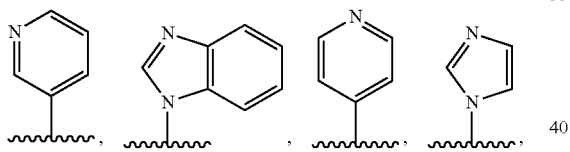

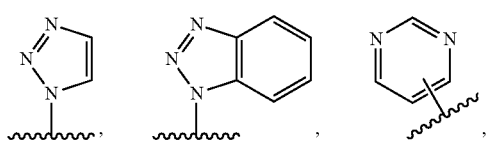

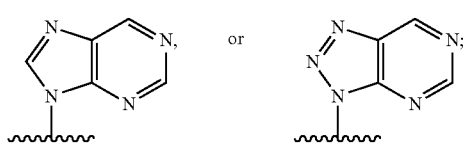

R³ is H or CH₃; and
R⁴ is H or CH₃.

In another embodiment, the AR targeting therapeutic agents of the present disclosure are ARi compounds of the formula (IV):

Formula (IV)

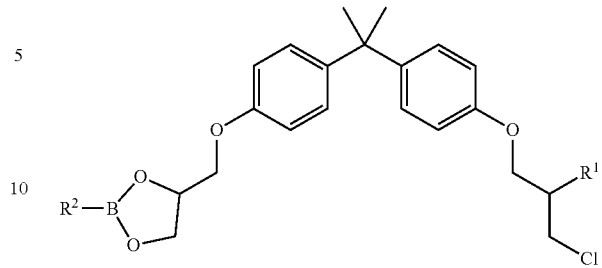

wherein:

R¹ is OH, OMe, F, CF₃, OCF₃, Cl, Br, (HO)₂B, KF₃B, NaF₃,

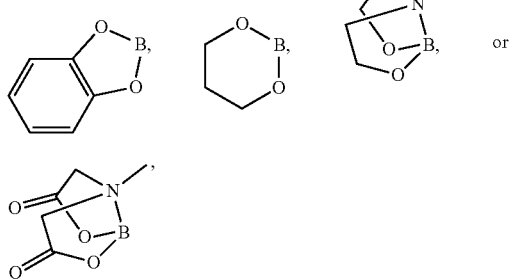

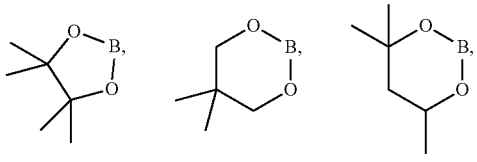

wherein if a boron atom is present in R¹ then the substituent point of attachment is on the boron atom;

R² is

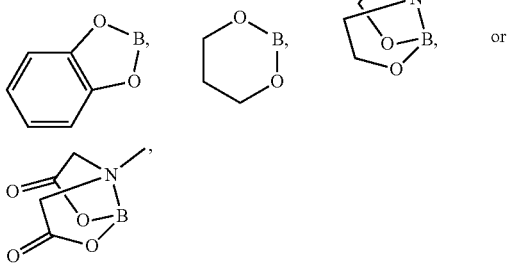 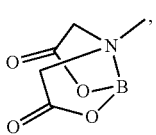

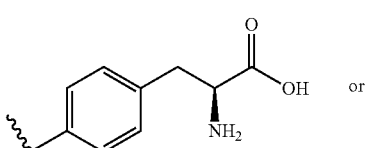

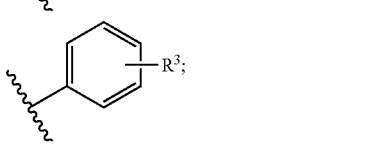

and

R³ is H, OH, CH₃, CF₃, F, Cl, Br, I, CN, B(OH)₂, OCH₃, OCF₃, CHF₂, CHCl₂, or CCl₃.

In another embodiment, the AR targeting therapeutic agents of the present disclosure are ARi compounds of the formula (V):

Formula V

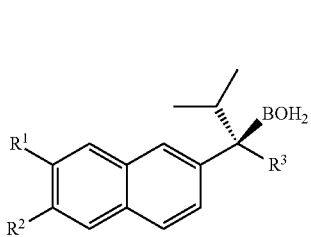

wherein

R¹ is —SCH₃, —SCHF₂, —SCF₃, —OCH₃, —OCHF₂, or —OCF₃;

R² is —SCH₃, —SCHF₂, —SCF₃, —OCH₃, —OCHF₂, or —OCF₃; and

R³ is

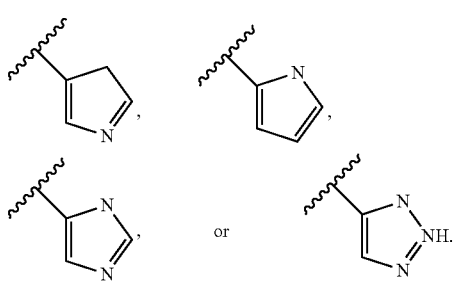

In another embodiment, the AR targeting therapeutic agents of the present disclosure are ARi compounds of the formula (V):

Formula VI

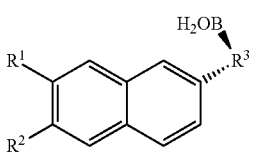

wherein

R¹ is H, CH3, OH, CF3, —OCH3, —OCF3, —OCHF2, —COCH3, or —CONHCH₃;

R² is H, CH3, OH, CF3, —OCH3, —OCF3, —OCHF2, —COCH3, or —CONHCH₃; and

R³ is

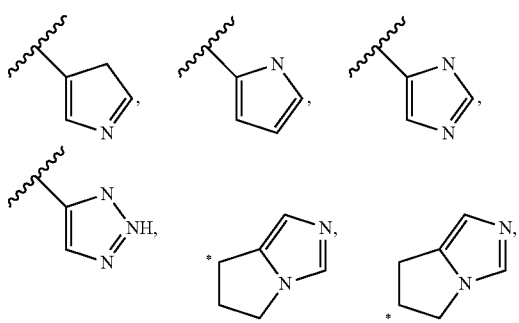

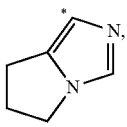 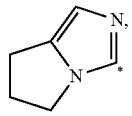

where * represents the point of attachment.

In another embodiment, the AR targeting therapeutic agents of the present disclosure are ARi compounds of the formula (VII):

Formula VII

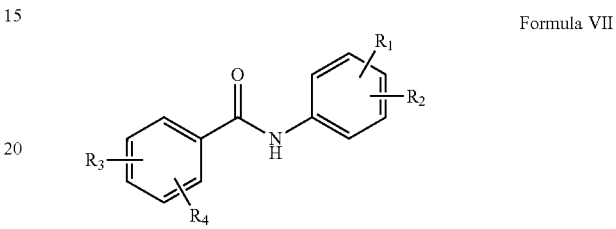

wherein

R¹ is H, OH, OMe, F, CN, CF₃, OCF₃, Cl, Br, (HO)₂B, KF₃B, NaF₃,

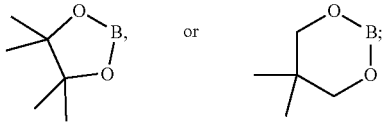

R² is NO₂, OH, OMe, F, CN, CF₃, OCF₃, Cl, Br, (HO)₂B, KF₃B, NaF₃,

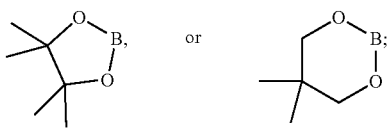

R³ is H, OH, OMe, F, CF₃, OCF₃, Cl, Br, (HO)₂B, KF₃B, NaF₃,

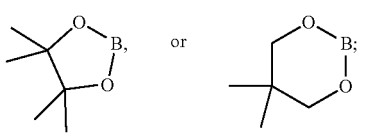

and

R⁴ is H, OH, OMe, F, difluoro-, CF₃, OCF₃, Cl, Br, (HO)₂B, KF₃B, NaF₃

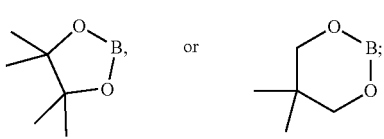

wherein if a boron atom is present in $R^1$, $R^2$, $R^3$, or $R^4$, then the substituent point of attachment is on the boron atom.

In a preferred embodiment, the inhibitor of formula (I) having the following structure, and is denoted ARi 1:

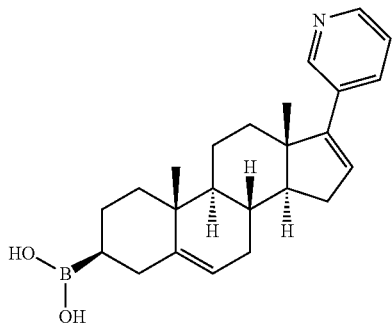

ARi 1

In a preferred embodiment, the ARi is a compound of formula (I) having the following structure, and denoted as ARi 2:

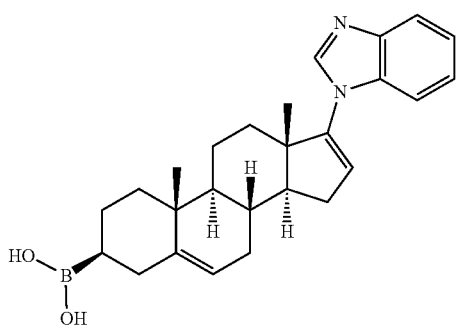

ARi 2

In a preferred embodiment, the ARi is a compound of formula (IV) having the following structure and denoted as ARi 3:

In a preferred embodiment, the ARi is a compound of formula (VII) having the following structure, and denoted as ARi 4:

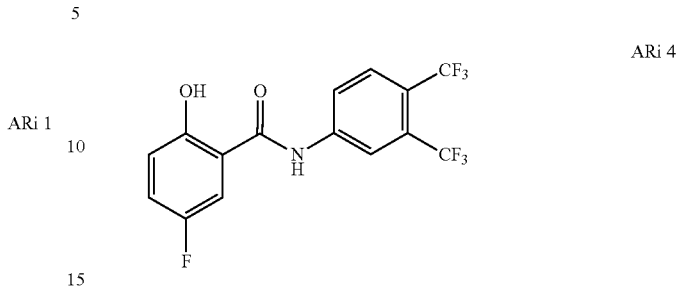

ARi 4

In a preferred embodiment, the ARi is a compound of formula (VII) having the following structure, and denoted as ARi 5:

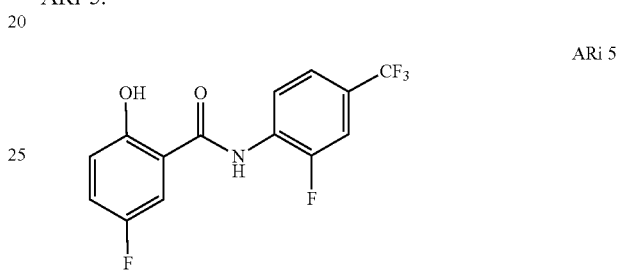

ARi 5

In a preferred embodiment, the ARi is a compound of formula (VII) having the following structure, and denoted as ARi 6:

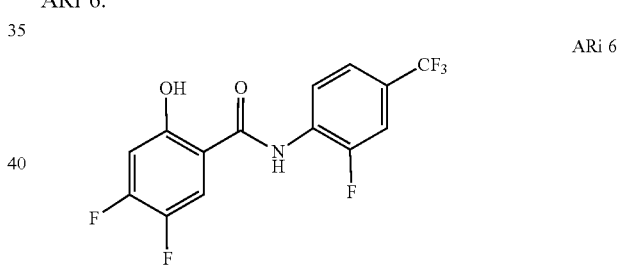

ARi 6

These and other features, aspects, and advantages of embodiments of the present disclosure will become better understood with regard to the following descriptions, claims, and accompanying drawings explained below.

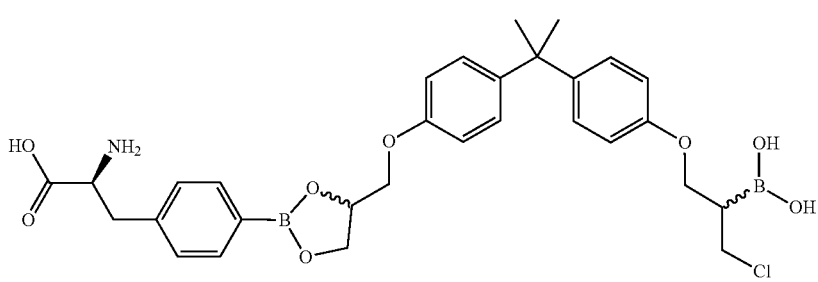

ARi3

In a preferred embodiment, the ARi is a compound of formula (VII) having the following structure, and denoted as ARi 11:

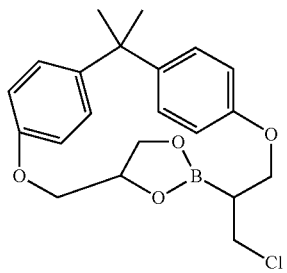

ARi 11

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Figure 1:
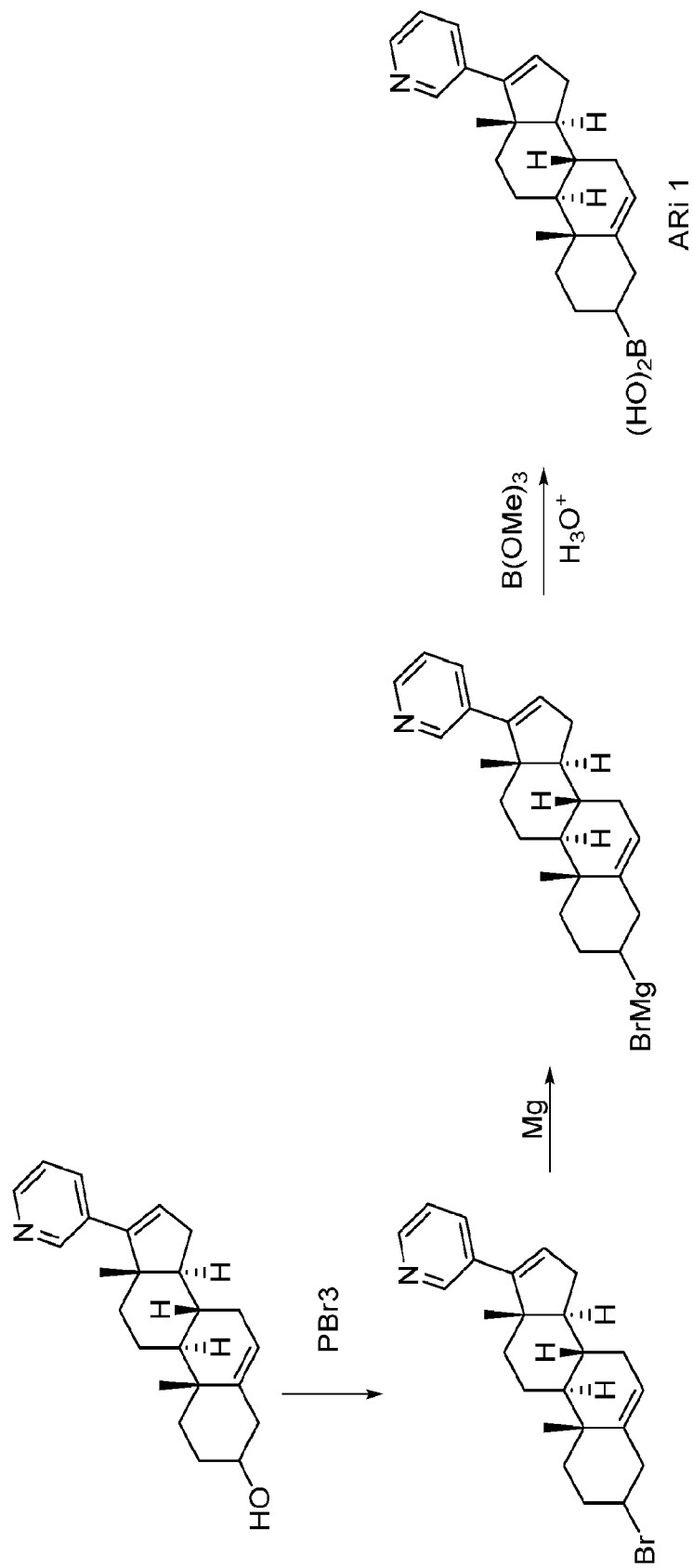
FIG. 1 shows the general synthetic scheme for preparation of ARi 1.

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

As used herein, the term "minimize" or "reduce", or derivatives thereof, include a complete or partial inhibition of a specified biological effect (which is apparent from the context in which the terms "minimize" or "reduce" are used).

In an embodiment, the disclosure provides for a pharmaceutical composition in the form of at least one ARi for treatment of proliferative diseases, including cancer, and in particular prostate cancer, that can obtain clinical benefits from hormone therapy that targets androgen receptor signaling. The composition may comprise at least one ARi in an amount that is therapeutically effective.

The disclosure therefore relates to use of an androgen receptor signaling inhibitor according to any compound of Formulas I, or combinations thereof, for treatment and prevention of proliferative diseases including cancer that can derive clinical benefits from such use.

The pharmaceutical compositions of the present disclosure can be in any form known to those of skill in the art. For instance, in some embodiments the pharmaceutical compositions are in a form of a product for oral delivery, said product form being selected from a group consisting of a concentrate, dried powder, liquid, capsule, pellet, and pill. In other embodiments, the pharmaceutical compositions of the disclosure are in the form of a product for parenteral administration including intravenous, intradermal, intramuscular, and subcutaneous administration. The pharmaceutical compositions disclosed herein may also further comprise carriers, binders, diluents, and excipients.

Also, in other aspects, the present disclosure relates to new compounds that inhibit androgen dependent disease progression and/or downregulate the androgen receptor, and their pharmaceutically acceptable salts; pharmaceutical compositions comprising the new ARi compounds, either alone or in combination with at least one additional therapeutic agent, with a pharmaceutically acceptable carrier, and uses of the new ARi compounds, either alone or in combination with at least one additional therapeutic agent, in the treatment of proliferative diseases including prostate cancer at any stage of the disease diagnosis. The combination with an additional therapeutic agent may take the form of combining the new ARi compounds with any known therapeutic agent.

Salts of the compounds according to the disclosure include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the disclosure is salts of the compounds according to the disclosure including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the disclosure is the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)-benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from $NH_3$ or organic amines having from 1 to 16 C-atoms such as, e.g., ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formulas (I) according to this disclosure as well as their salts may contain, e.g., when isolated in crystalline form, varying amounts of solvents. Included within the scope of the disclosure are therefore all solvates and in particular all hydrates of the compounds of formula (I) according to this disclosure as well as all solvates and in particular all hydrates of the salts of the compounds of formula (I) according to this disclosure. In the context of the invention, solvates refer to those forms of the compounds according to the invention which, in the solid or liquid state, form a complex by coordination with solvent molecules. Hydrates are a specific form of solvates in which the coordination is with water.

The compounds according to the disclosure and their salts can exist in the form of tautomers which are included in the embodiments of the disclosure.

The compounds of the disclosure may, depending on their structure, exist in different stereoisomeric forms. These forms include configurational isomers or optionally conformational isomers (enantiomers and/or diastereoisomers including those of atropisomers). The present disclosure therefore includes enantiomers, diastereoisomers as well as mixtures thereof. From those mixtures of enantiomers and/or disasteroisomers pure stereoisomeric forms can be isolated with methods known in the art, preferably methods of chromatography, especially high pressure liquid chromatography (HPLC) using achiral or chiral phase. The disclosure further includes all mixtures of the stereoisomers mentioned above independent of the ratio, including the racemates.

Some of the compounds and salts according to the disclosure may exist in different crystalline forms (polymorphs) which are within the scope of the disclosure.

It is a further object of the disclosure to provide compounds that inhibit androgen receptor signaling, methods of synthesizing the ARi compounds, methods of manufacturing the ARi compounds, and methods of using the ARi compounds.

Another object of the disclosure is to provide a composition, for example a pharmaceutical composition, comprising at least one ARi compound in an amount effective for the indication of proliferative diseases such as cancer, including but not limited to endocrine related cancer, for treatment and prevention of recurrence.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development, recurrence, or progression of such states and/or the symptoms of such states.

The treatment or prevention of a disease, a condition, a disorder, an injury or a health problem may be partial or complete.

A further object of the disclosure is a kit, comprising a composition containing at least one ARi for treatment and prevention of cancer and cancer related morbidities. The composition of the kit may comprise at least one carrier, at least one binder, at least one diluent, at least one excipient, at least one other therapeutic agent, or mixtures thereof.

The methods for treating a clinical indication by the ARi compounds disclosed herein, may be effectuated by administering a therapeutically effective amount of the ARi to a patient in need thereof, this therapeutically effective amount may comprise administration of the prodrug to the patient at 1 mg/kg/day, 2 mg/kg/day, 3 mg/kg/day, 4 mg/kg/day, 5 mg/kg/day, 10 mg/kg/day and 20 mg/kg/day. Alternatively, amounts ranging from about 0.001 mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to 10 mg/kg/day, or about 10 mg/kg/day to about 100 mg/kg/day are also contemplated.

In certain aspects, the at least one boron-based prodrug analog has a purity of ≥75%, ≥80%, ≥85%, ≥90%, ≥95%, ≥96%, ≥97%, or ≥98%, and preferably ≥99%.

One aspect of the present disclosure is the compounds disclosed herein as well as the intermediates as used for their synthesis.

While certain features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is expressly stated as being "critical" or "essential."

Figure 2:
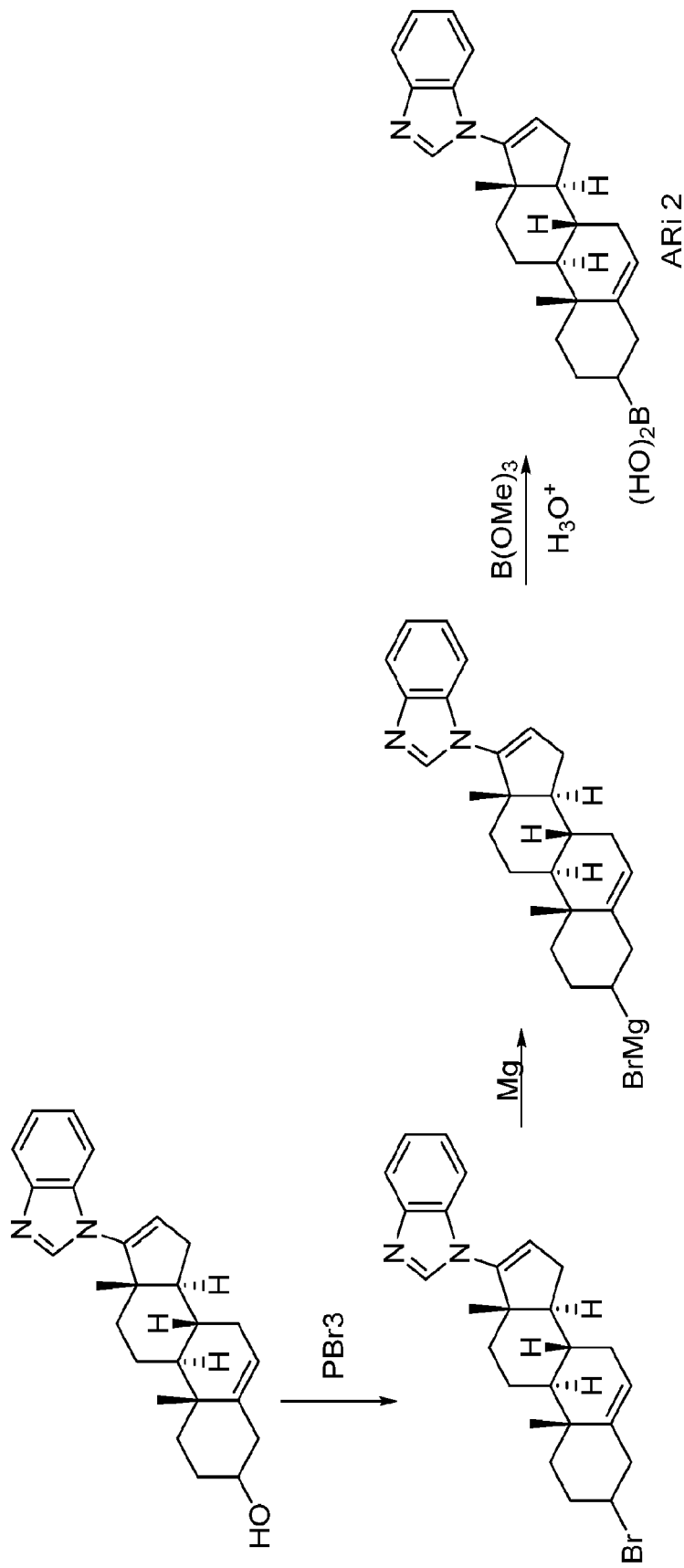
FIG. 2 shows the general synthetic scheme for preparation of ARi 2.
Figure 3:
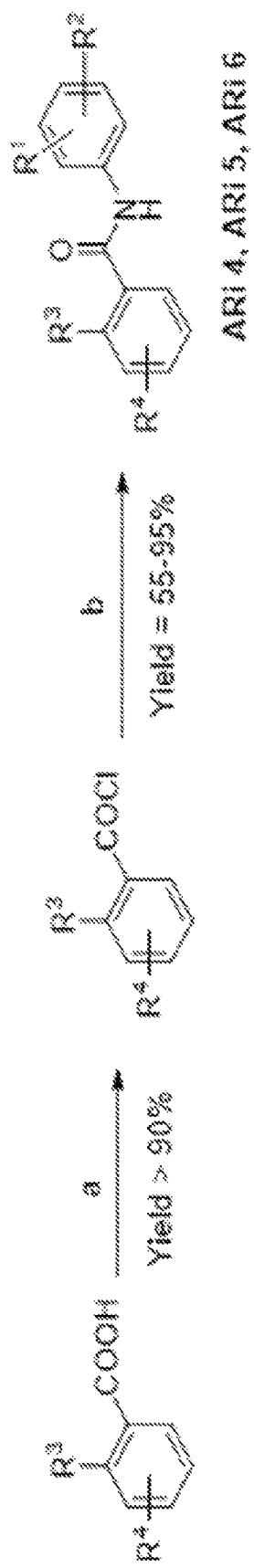
FIG. 3 shows the general synthetic scheme for preparation of selected ARi compounds of formula VII. Reactants and reaction conditions: (a) Thionyl chloride, DMF (cat.), anhydrous THF, 0° C.—r.t.; (b) Substituted anilines, DMAP (cat.), anhydrous THF, 0° C.—r.t. Synthetic scheme for the preparation of ARi 4-6 with details as follows: to the solution of substituted benzoic acid (1.00 mmol) in anhydrous THF (15 mL) was added solution of $SOCl_2$ in anhydrous THF (5 mL dissolved in 5 mL anhydrous THF) dropwise at 0° C. under $N_2$. The reaction mixture was stirred at r.t. for 1.5 h. The solvent was removed by reduced pressure distillation to obtain white to off-white solid or semi-solid. The residue was dissolved in anhydrous THF (10 mL), and added to the mixture of substituted aniline and DMAP (cat.) in anhydrous THF dropwise at 0° C. under $N_2$. The reaction mixture was stirred at r.t. for 1.5 h or overnight. The solvent was removed under vacuum. The residue was suspended in ethyl acetate (EA) (10 mL) and washed with HCl (aq., 2M), saturated $NaHCO_3$ (aq.), and saturated NaCl (aq.). The organic fraction was dried over $MgSO_4$, concentrated and purified by flash column chromatography on silica gel with a gradient eluent of hexane and EA.
Figure 4:
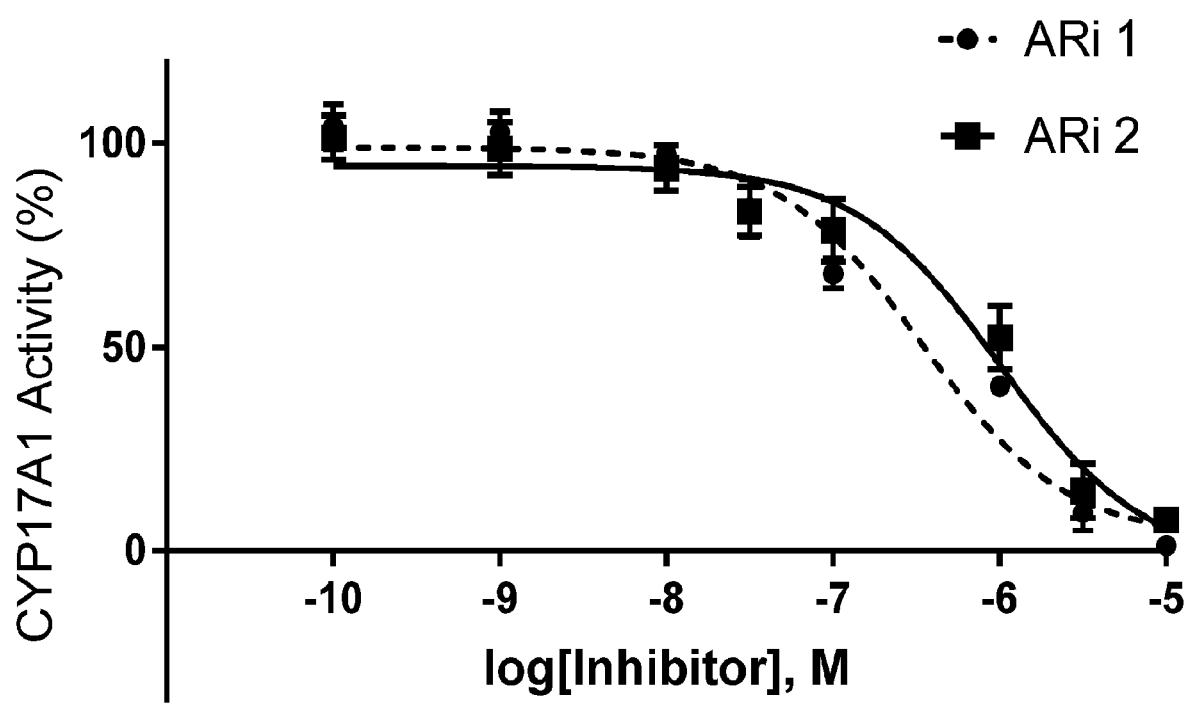
FIG. 4 shows the inhibitory effect of ARi 1 and ARi 2 on CYP17A1 activity.
Figure 5:
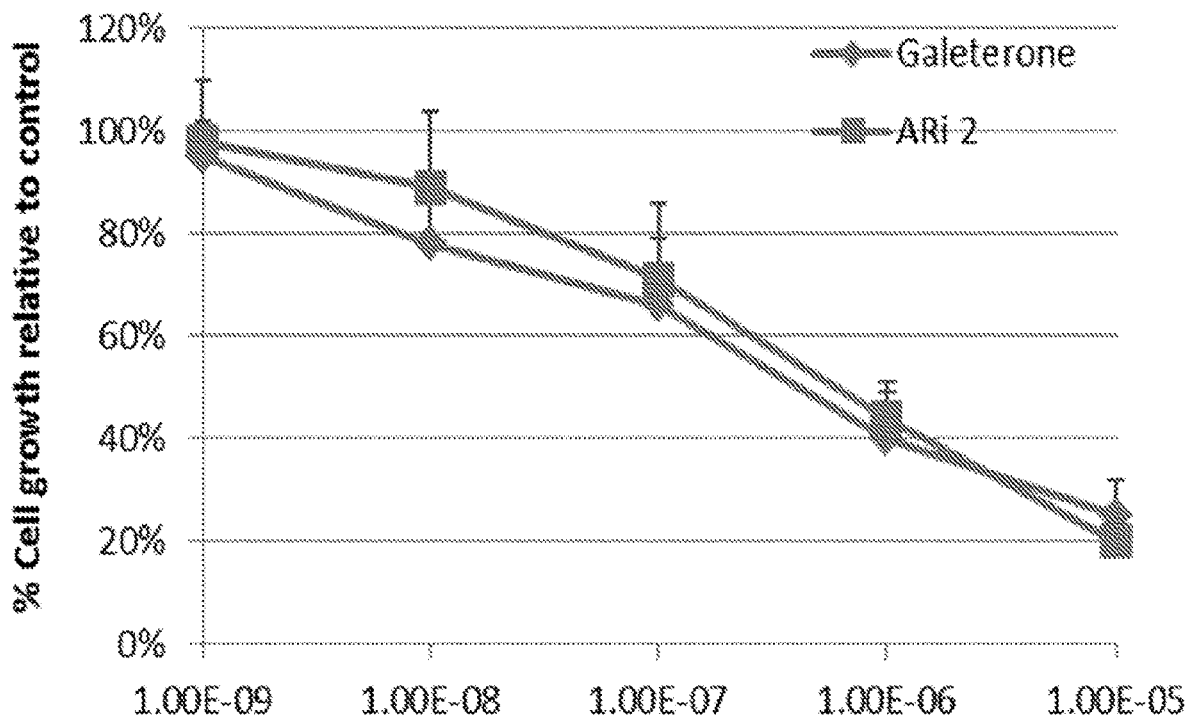
FIG. 5 shows the effect of ARi 2 and galeterone on growth of human prostate adenocarcinoma cells (LNCaP cells) at various treatment doses.
Figure 6:
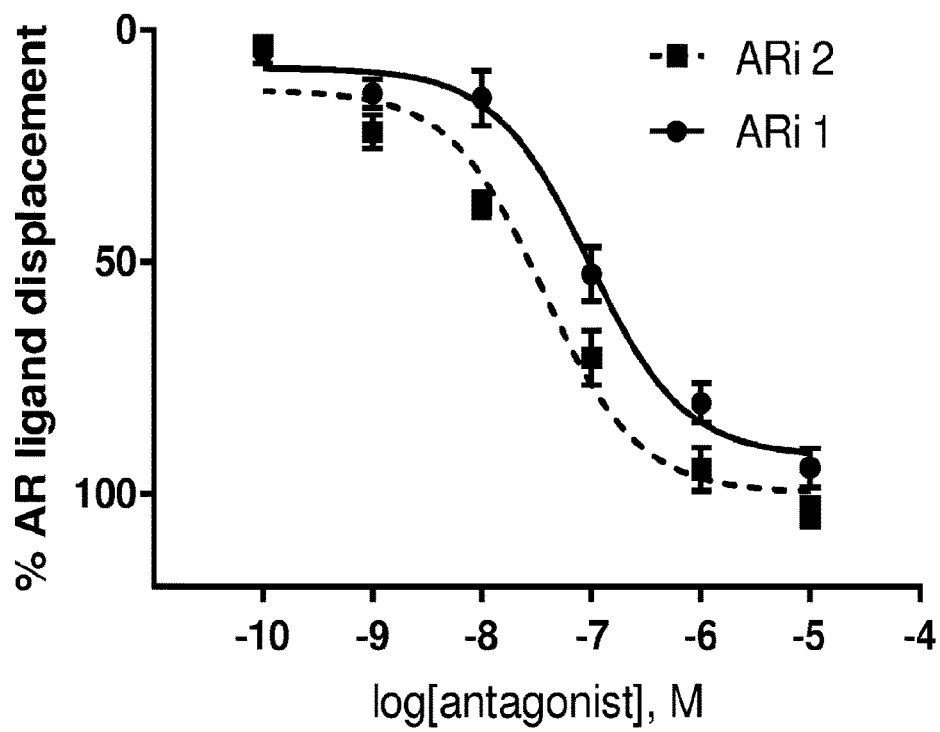
FIG. 6 shows competitive binding of ARi 1 and ARi 2 to full-length androgen receptor (AR).
Figure 7:
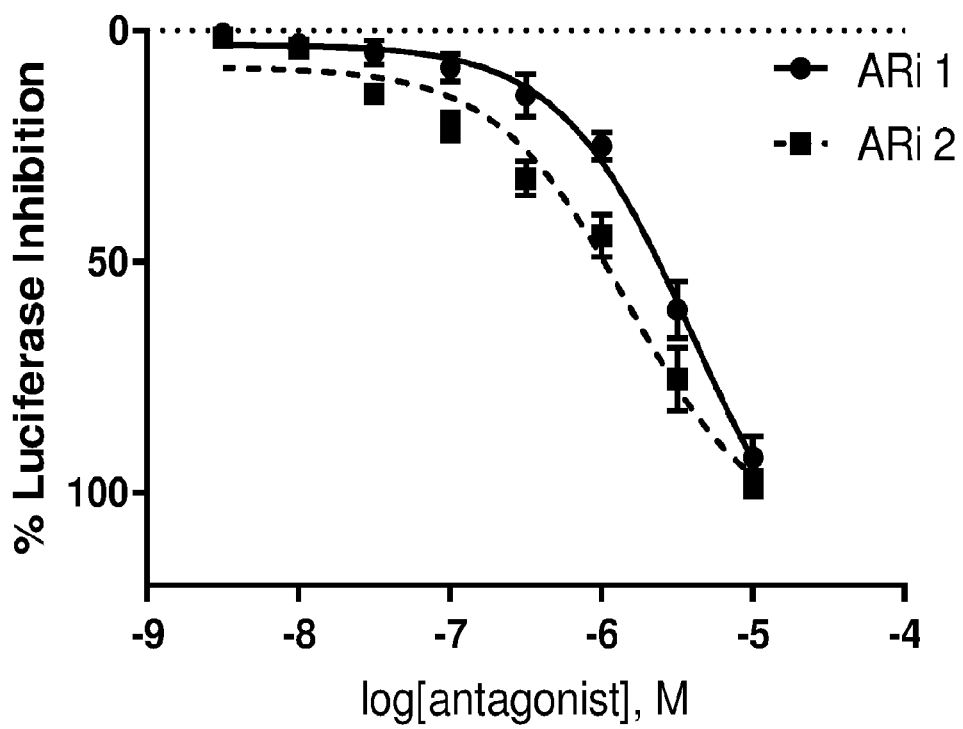
FIG. 7 shows the antagonistic effects of ARi 1 and ARi 2 in LNCaP prostate cancer cells.
Figure 8:
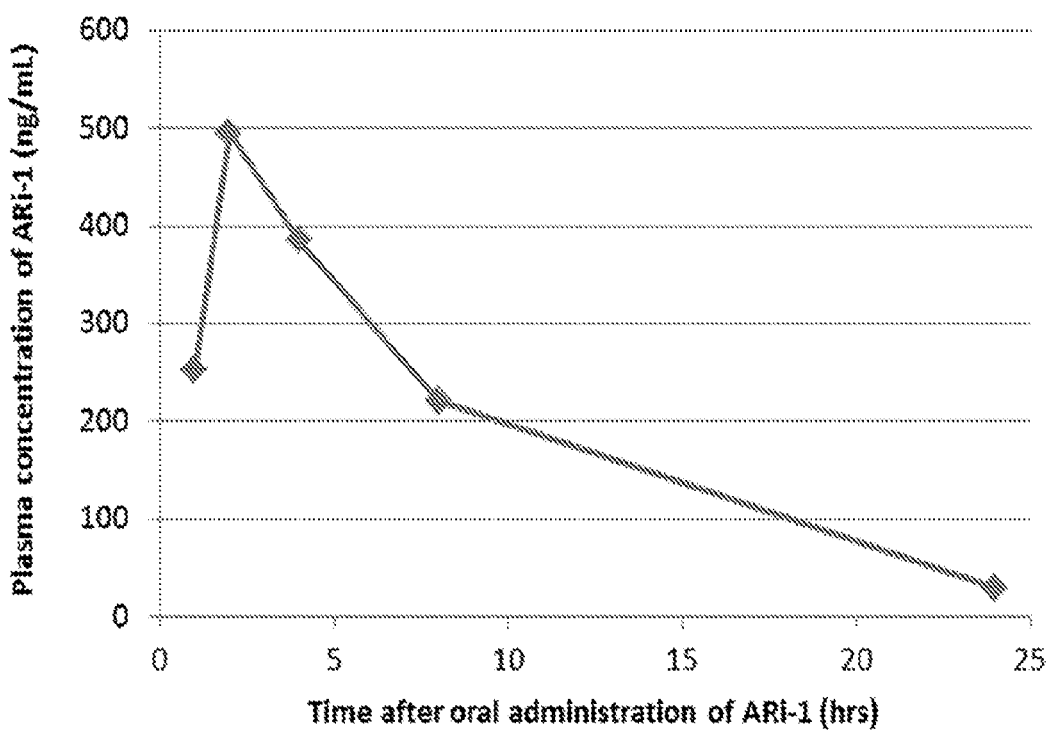
FIG. 8 shows the oral bioavailability of ARi 1 in rats after a single dose of 5 mg/kg PO.
Figure 9:
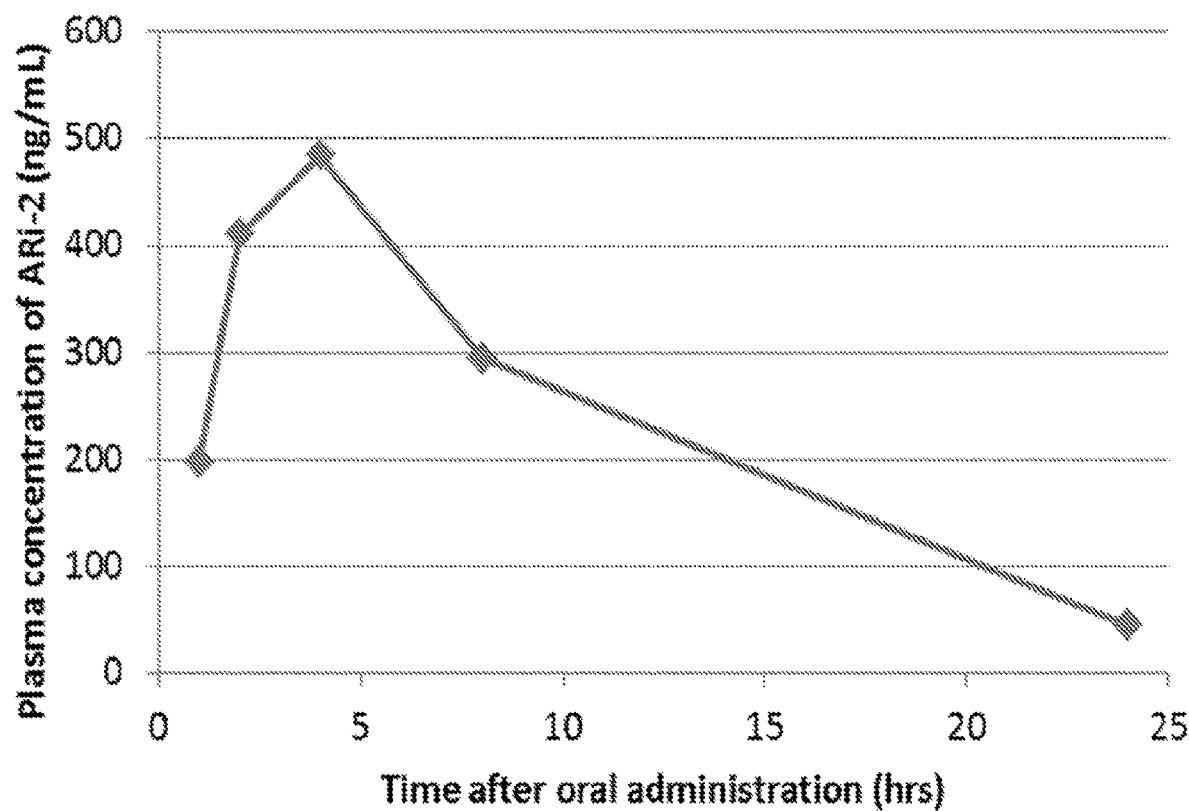
FIG. 9 shows the oral bioavailability of ARi 2 in rats after a single dose of 5 mg/kg PO.
Figure 10:
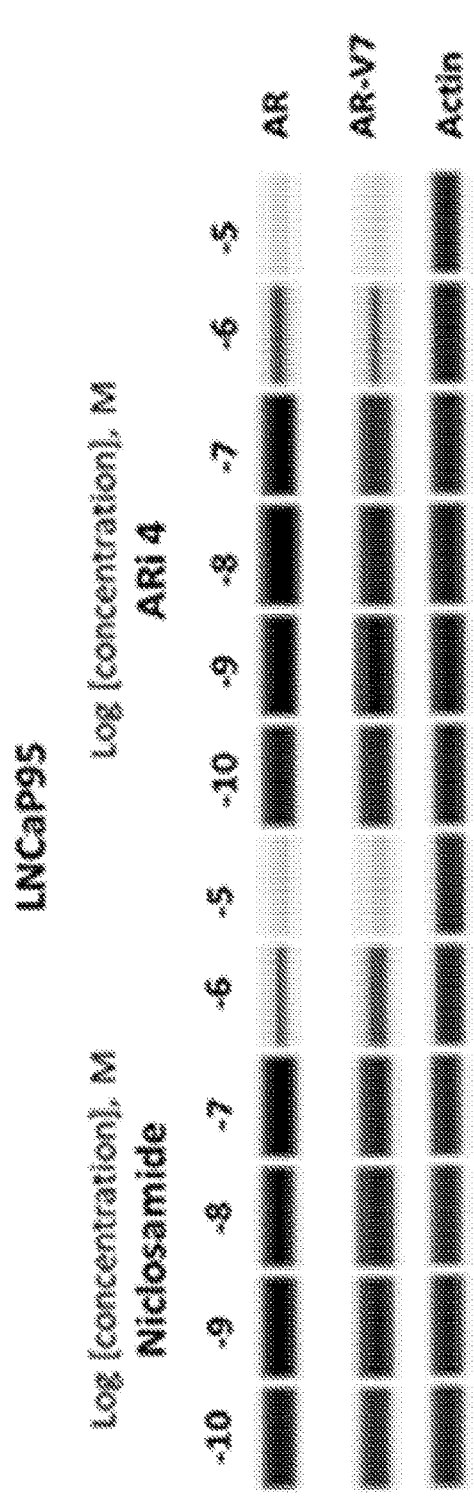
FIG. 10 shows dose-dependent downregulation of AR and AR-V7 by ARi 4 (of formula VII) and niclosamide in LNCaP95, an enzalutamide-resistant prostate cancer cell line.
Figure 10:
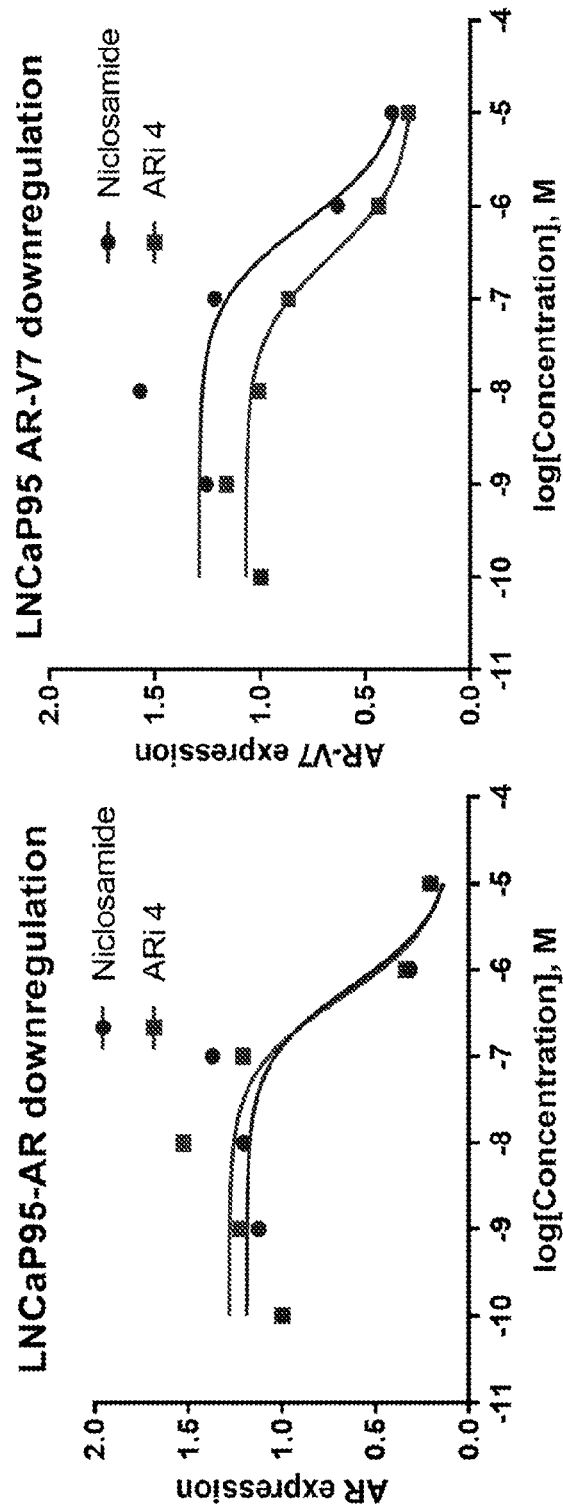
Figure 11:
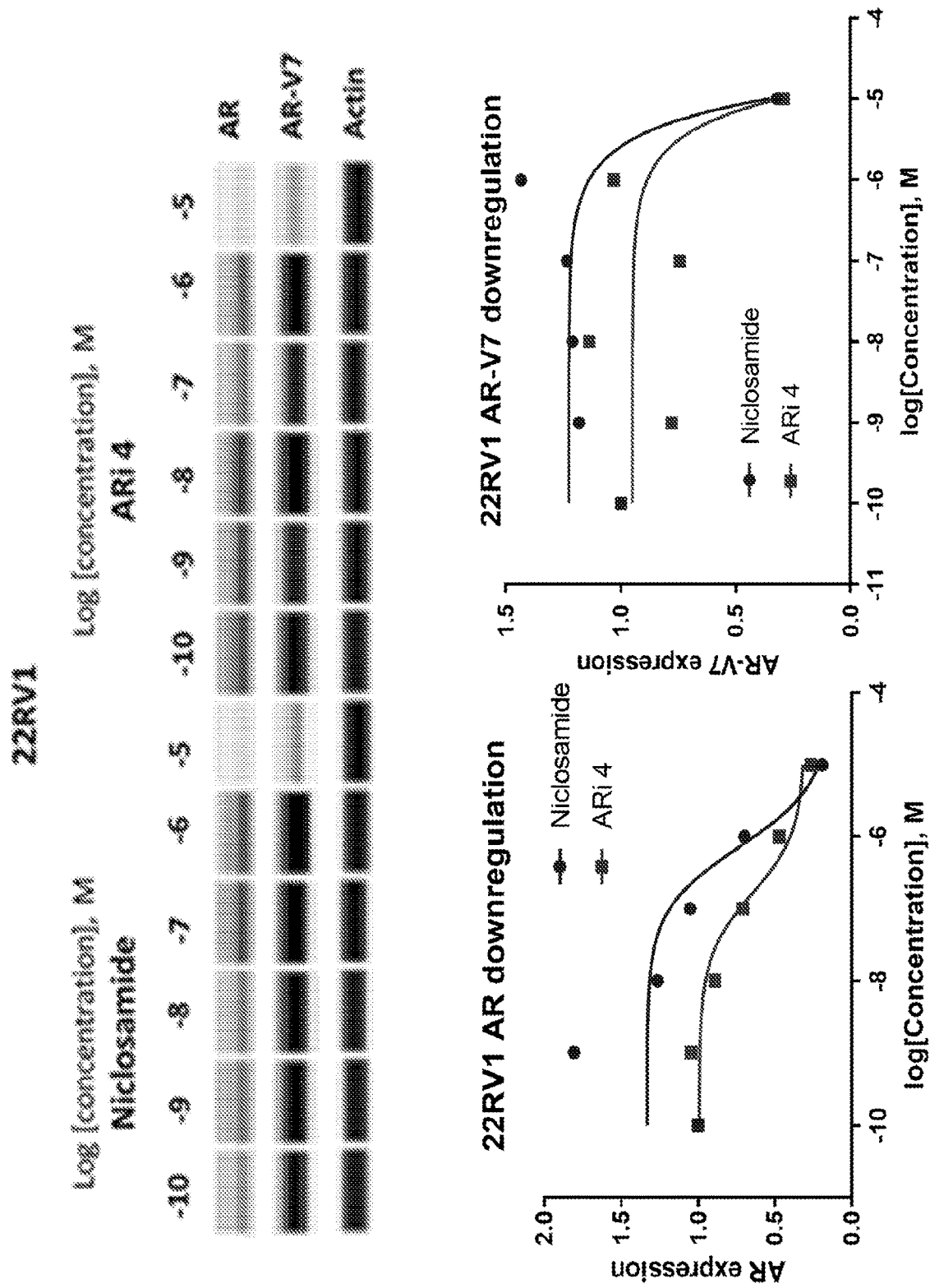
FIG. 11 shows dose-dependent downregulation of AR and AR-V7 by ARi 4 (of formula VII) and niclosamide in 22RV1, an enzalutamide-resistant prostate cancer cell line.
Figure 12:
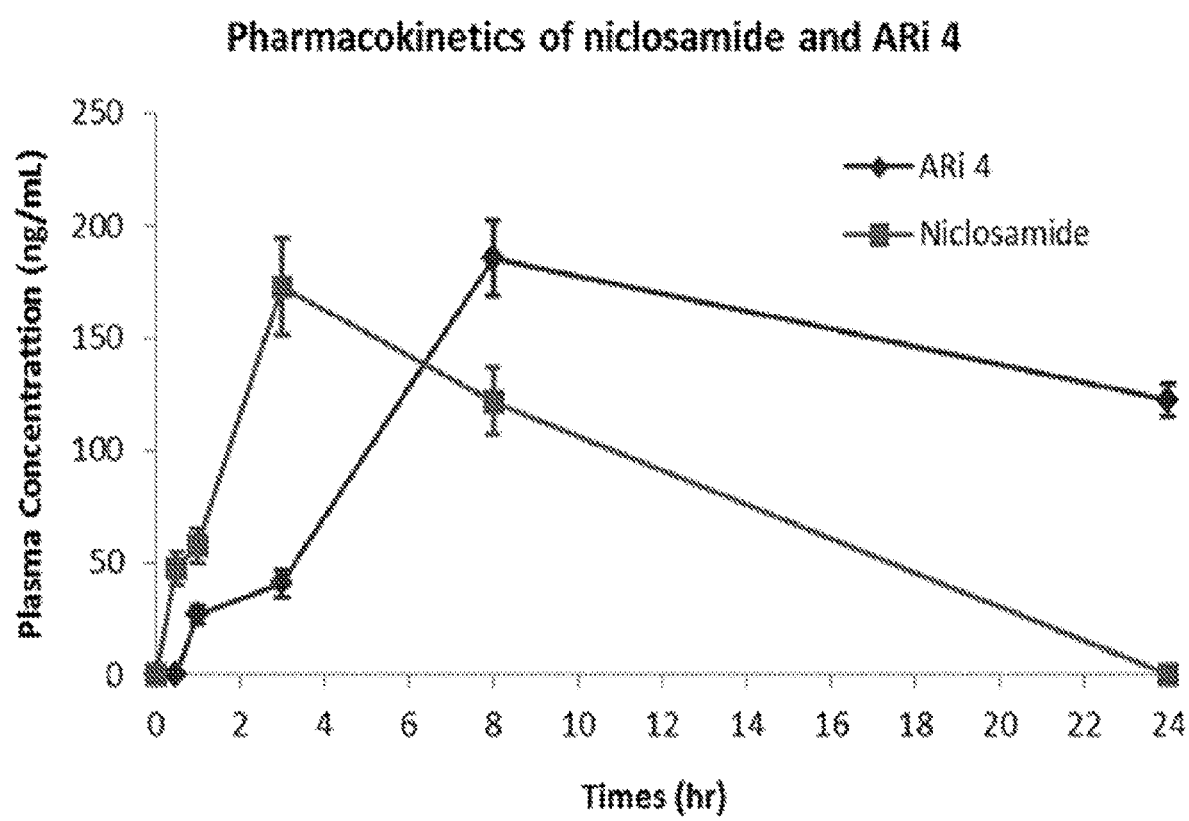
FIG. 12 shows the pharmacokinetic profile of ARi 4 and niclosamide plasma concentration in Sprague Dawley rats after a single oral dose of 10 mg/kg.

The compounds according to the disclosure can be prepared according to the schemes shown in FIGS. 1-3.

The compounds according to the disclosure are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present disclosure which possess a sufficiently basic or acidic functionality, may result in the formation of a salt, such as, in the case of a compound of the present disclosure which is sufficiently basic, a trifluoroacetate or formate salt for example, or, in the case of a compound of the present disclosure which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present disclosure may not fully remove traces of cosolvents, especially such as formic acid or trifluoroacetic acid, to give solvates or inclusion complexes. The person skilled in the art will recognize which solvates or inclusion complexes are acceptable to be used in subsequent biological assays. It is to be understood that the specific form (e.g., salt, free base, solvate, inclusion complex) of a compound of the present disclosure as isolated as described herein is not necessarily the only form in which said compound can be applied to a biological assay in order to quantify the specific biological activity.

Salts of the compounds of formulas (I) through (VII) according to the disclosure can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

LNCaP95 and 22RV1 are prostate cancer cell lines that express high level of AR-V7 and other AR-Vs, and are enzalutamide-resistant. LNCaP95 cells were maintained in RPMI1640 medium with charcoal-stripped serum (CSS). 22Rv1 cells were maintained in RPMI1640 medium with 10% FBS. Cells were seeded in 96-well plates ($5\times10^3$ cells/well) containing 50 μL growth medium for 24 hrs. After medium removal, 100 μL fresh medium containing individual compound at different concentrations was added to each well and incubated at 37° C. for 72 h. Then 20 μL of resazurin was added for 2 h before recording fluorescence at 560 nm (excitation) and 590 nm (emission) using a Victor microtiter plate fluorometer (Perkin-Elmer, USA). The IC50 was defined as the compound concentration required for inhibiting cell proliferation by 50%, in comparison with cells treated with the maximum amount of DMSO (0.25%) and considered as 100% viability.

Table 1 shows the antiproliferative activities of compounds of formula VII against enzalutamide-resistant prostate cancer cells, compared with niclosamide.

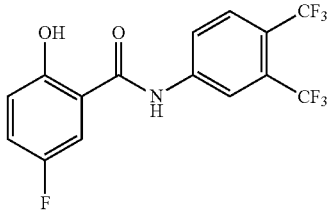

| Formula VII | Substitution Groups | | | | | IC$_{50}$ (μM) | |
|---|---|---|---|---|---|---|---|
| | R$^1$ | R$^2$ | R$^3$ | R$^4$ | Inhibitory rate at $10^{-6}$ M in 22RV1 cells | LCaP95 | 22RV1 |
| Niclosamide | 4'-NO$_2$ | 2'-Cl | 2-OH | 5-Cl | 51.3% | 0.372 | 0.284 |
| ARi 4 | 3'-CF$_3$ | 4'-CF$_3$ | 2-OH | 5-F | 15.7% | 0.130 | 0.0997 |

| Formula VII | R¹ | R² | R³ | R⁴ | Inhibitory rate at 10⁻⁶ M in 22RV1 cells | IC₅₀ (μM) LCaP95 | 22RV1 |
|---|---|---|---|---|---|---|---|
| ARi 5 | 4'-CF₃ | 2'-F | 2-OH | 5-F | 12.4% | 0.152 | 0.121 |
| ARi 6 | 4'-CF₃ | 2'-F | 2-OH | 4,5-diF | 52.7% | 0.199 | 0.382 |
| ARi 7 | 4'-CF₃ | 2'-Cl | 2-OH | 5-F | 14.5% | 0.148 | 0.135 |
| ARi 8 | 4'-CF₃ | 3'-CN | 2-OH | 5-F | 21.8% | 0.161 | 0.195 |
| ARi 9 | 4'-CN | 2'-F | 2-OH | 5-F | 55.3% | 0.397 | 0.414 |

| Formula VII | Substitution Groups | | | | IC$_{50}$ (μM) | |
|---|---|---|---|---|---|---|
| (structure with R$_1$, R$_2$, R$_3$, R$_4$) | R$^1$ | R$^2$ | R$^3$ | R$^4$ | Inhibitory rate at 10$^{-6}$ M in 22RV1 cells | LCaP95 | 22RV1 |
| ARi 10 (structure) | 4'-NO$_2$ | 2'-F | 2-OH | 5-F | 43.9% | 0.206 | 0.244 |

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only, the scope of the present disclosure is to be limited only by the following claims.

REFERENCES CITED

1. Siegel R, Naishadham D, Jemal A. Cancer statistics, 2013. CA Cancer J Clin. 2013 January; 63(1):11-30. doi: 10.3322/caac.21166.
2. Attard G, Richards J, de Bono J S. New strategies in metastatic prostate cancer: targeting the androgen receptor signaling pathway. Clin Cancer Res. 2011 Apr. 1; 17(7):1649-57. doi: 10.1158/1078-0432.CCR-10-0567. Review. PubMed PMID: 21372223; PubMed Central PMCID: PMC3513706.
3. Carver B S. Strategies for targeting the androgen receptor axis in prostate cancer. Drug Discov Today. 2014 September; 19(9):1493-7. doi: 10.1016/j.drudis.2014.07.008. Review. PubMed PMID: 25107669.
4. Hoang D T, Iczkowski K A, Kilari D, See W, Nevalainen M T. Androgen receptor-dependent and -independent mechanisms driving prostate cancer progression: Opportunities for therapeutic targeting from multiple angles. Oncotarget. 2016 Oct. 10. doi: 10.18632/oncotarget.12554. [Epub ahead of print] PubMed PMID: 27741508.
5. Lieberman R. Androgen deprivation therapy for prostate cancer chemoprevention: current status and future directions for agent development. Urology. 2001, August; 58(2 Suppl 1):83-90.
6. Dhawan M, Ryan C J. Utility of novel androgen receptor therapies in the real world: A nuanced approach. Urol Oncol. 2016 August; 34(8):340-7. doi: 10.1016/j.urolonc.2016.05.002. Review. PubMed PMID: 27450893.
7. Graham L, Schweizer M T. Targeting persistent androgen receptor signaling in castration-resistant prostate cancer. Med Oncol. 2016 May, 33(5):44. doi: 10.1007/s12032-016-0759-3. Review. PubMed PMID: 27042852.
8. Crona D J, Milowsky M I, Whang Y E. Androgen receptor targeting drugs in castration-resistant prostate cancer and mechanisms of resistance. Clin Pharmacol Ther. 2015 December; 98(6):582-9. doi: 10.1002/cpt.256. Review. PubMed PMID: 26331358; PubMed Central PMCID: PMC4715745.
9. Modena A, Ciccarese C, Fantinel E, Bimbatti D, Tortora G, Massari F. Metastatic castration-resistant prostate cancer: targeting the mechanisms of resistance to abiraterone acetate and enzalutamide. Expert Rev Anticancer Ther. 2015; 15(9):1037-48. doi: 10.1586/14737140.2015.1063423. Review. PubMed PMID: 26134919.
10. Reichert Z R, Hussain M. Androgen Receptor and Beyond, Targeting Androgen Signaling in Castration-Resistant Prostate Cancer. Cancer J. 2016 September/October; 22(5):326-329. PubMed PMID: 27749325.
11. Imamura Y, Sadar M D. Androgen receptor targeted therapies in castration-resistant prostate cancer: Bench to clinic. Int J Urol. 2016 August; 23(8):654-65.
12. Mostaghel E A, Marck B T, Plymate S R, Vessella R L, Balk S, Matsumoto A M, et al. Resistance to CYP17A1 inhibition with abiraterone in castration-resistant prostate cancer: induction of steroidogenesis and androgen receptor splice variants. Clin Cancer Res 2011; 17:5913-25.
13. Galletti G, Leach B I, Lam L, Tagawa S T. Mechanisms of resistance to systemic therapy in metastatic castration-resistant prostate cancer. Cancer Treat Rev. 2017 June; 57:16-27.
14. Bubley G J, Balk S P. Association Between Androgen Receptor Splice Variants and Prostate Cancer Resistance to Abiraterone and Enzalutamide. J Clin Oncol. 2017 Jul. 1; 35(19):2103-2105.

15. Antonarakis E S, Lu C, Wang H, Luber B, Nakazawa M, Roeser J C, Chen Y, Mohammad T A, Chen Y, Fedor H L, Lotan T L, Zheng Q, De Marzo A M, Isaacs J T, Isaacs W B, Nadal R, Paller C J, Denmeade S R, Carducci Mass., Eisenberger M A, Luo J. AR-V7 and resistance to enzalutamide and abiraterone in prostate cancer. N Engl J Med. 2014, Sep. 11; 371(11):1028-38.

16. Schrader A J, Schrader M G, Cronauer M V. Re: androgen receptor splice variants mediate enzalutamide resistance in castration-resistant prostate cancer cell lines. Eur Urol 2013; 64:169-70.

17. Zhang X, Morrissey C, Sun S, Ketchandji M, Nelson P S, True L D, et al. Androgen receptor variants occur frequently in castration resistant prostate cancer metastases. PLoS One 2011; 6:e27970.

18. Sun S, Sprenger C C, Vessella R L, Haugk K, Soriano K, Mostaghel E A, et al. Castration resistance in human prostate cancer is conferred by a frequently occurring androgen receptor splice variant. J Clin Invest 2010; 120:2715-30.

What is claimed is:

1. A compound of Formula (I):

Formula I

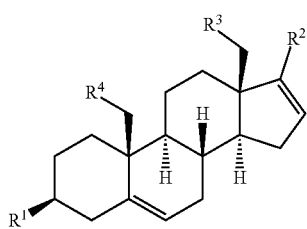

wherein:

$R^1$ is $(HO)_2B$,

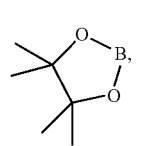 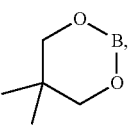 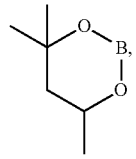

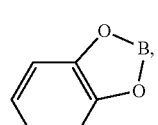 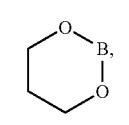 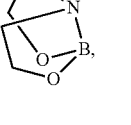 or

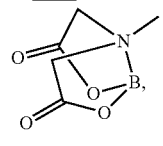

wherein in $R^1$ the substituent point of attachment is on the boron atom;

$R^2$ is

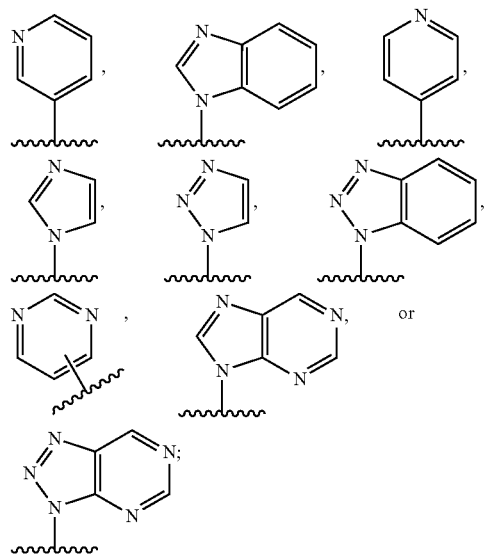

$R^3$ is H; and $R^4$ is H.

2. A method of inhibiting androgen receptor (AR) signaling in a mammal in need thereof, comprising administering an effective amount of the compound of claim 1 to the mammal.

3. A method of making a medicament for the treatment and/or prophylaxis of diseases comprising combining the compound of claim 1 with an inert, nontoxic, pharmaceutically suitable excipient.

4. A method of treatment and/or prophylaxis of a proliferative disease in a patient in need thereof, comprising administering a therapeutically effective amount of the compound of claim 1 to the patient, wherein the cancer is prostate cancer.

5. The compound of claim 1, wherein:

$R^1$ is $(HO)_2B$.

6. The compound of claim 1, wherein:

$R^1$ is

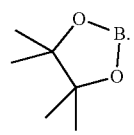

7. The compound of claim 1, wherein:

$R^1$ is

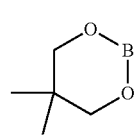

8. The compound of claim 1, wherein:
R² is

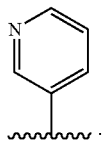 [SMILES: *c1cccnc1]

9. The compound of claim 1, wherein:
R² is

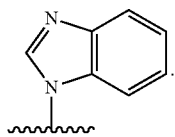

10. The compound of claim 1, wherein:
R² is

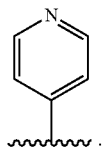 [SMILES: *c1ccncc1]

11. The compound of claim 1, wherein:
R² is

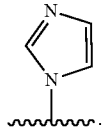 [SMILES: *n1ccnc1]

12. The compound of claim 1, wherein:
R² is

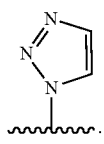

13. The compound of claim 1, wherein:
R² is

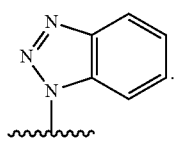

14. The compound of claim 1, wherein:
R² is

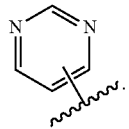

15. The compound of claim 1, wherein:
R² is

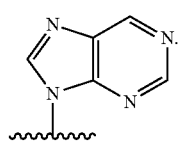 [SMILES: *n1cnc2cncnc21]

16. The compound of claim 1, wherein:
R² is

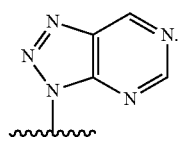 [SMILES: *n1nnc2cncnc21]

17. The compound of claim 1, wherein:
R¹ is

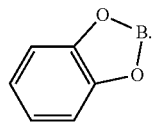

18. The compound of claim 1, wherein:
R¹ is

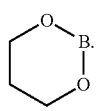

19. The compound of claim 1, wherein:
R¹ is

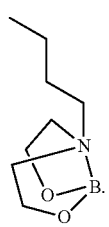

20. The compound of claim 1, wherein:
R¹ is
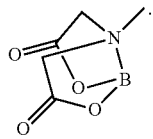
21. The compound of claim 1, wherein:
R¹ is
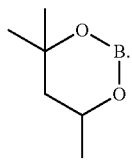
* * * * *